United States Patent [19]

Ueda et al.

[11] Patent Number: 4,735,952
[45] Date of Patent: Apr. 5, 1988

[54] ARYLTHIO PIPERIDINAMIDE OF (4-QUINOLINYLAMINO)BENZOIC ACID AND S-OXIDIZED DERIVATIVES

[75] Inventors: Ikuo Ueda, Uenohigashi; Masaaki Matsuo, Toyonaka; Kiyoshi Taniguchi, Nagarahigashi; Takatomo Ogahara, Minoo, all of Japan

[73] Assignee: Fujisawa Pharmaceutical Co., Ltd., Osaka, Japan

[21] Appl. No.: 821,974

[22] Filed: Jan. 24, 1986

[30] Foreign Application Priority Data

Feb. 11, 1985 [GB] United Kingdom ............... 8503416
Jul. 12, 1985 [GB] United Kingdom ............... 8517675

[51] Int. Cl.$^4$ .................. C07D 215/46; C07D 403/12; A61K 31/47
[52] U.S. Cl. .................................... 514/313; 546/161; 546/193; 546/212; 546/216; 546/221; 546/226; 546/242; 546/14
[58] Field of Search ............... 514/311, 313; 544/363, 544/365; 546/159, 160, 161

[56] References Cited

U.S. PATENT DOCUMENTS

| | | | |
|---|---|---|---|
| 4,166,853 | 9/1979 | McCall et al. | 514/313 |
| 4,167,567 | 7/1979 | McCall et al. | 514/253 |
| 4,357,333 | 11/1982 | Archibald et al. | 514/313 |

FOREIGN PATENT DOCUMENTS

| | | | |
|---|---|---|---|
| 2559104 | 7/1976 | Fed. Rep. of Germany | 546/161 |
| 226877 | 11/1985 | Japan . | |
| 1268469 | 3/1972 | United Kingdom . | |
| 1416872 | 12/1975 | United Kingdom . | |

Primary Examiner—Donald G. Daus
Assistant Examiner—E. Bernhardt
Attorney, Agent, or Firm—Oblon, Fisher, Spivak, McClelland & Maier

[57] ABSTRACT

This invention provides a piperidine compound of the formula:

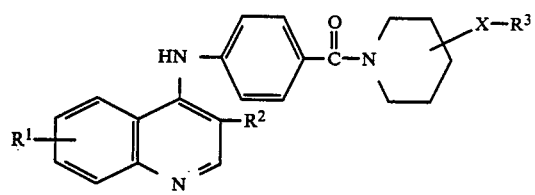

wherein
$R^1$ is hydrogen or trihalomethyl,
$R^2$ is hydrogen or protected carboxy,
$R^3$ is heterocyclic group or aryl which may be halogen substituted, and
X is —S—,

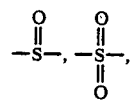

—O—, —NH— or lower alkylene which may be hydroxy substituted, and pharmaceutically acceptable salt thereof, These compounds possess hypotensive activity and are useful as anti-hypertensive agents. The invention further relates to processes for the preparation of these compounds and pharmaceutical compositions comprising compounds of the above formula.

10 Claims, No Drawings

ARYLTHIO PIPERIDINAMIDE OF (4-QUINOLINYLAMINO)BENZOIC ACID AND S-OXIDIZED DERIVATIVES

This invention relates to new piperidine compounds. More particularly, it relates to new piperidine compounds and pharmaceutically acceptable salt thereof which have an antihypertensive activity, to a process for the preparation thereof, and to pharmaceutical compositions comprising the same.

Accordingly, it is an object of this invention to provide new piperidine compounds and pharmaceutically acceptable salts thereof which are useful as antihypertensive agents.

Another object of this invention is to provide a process for the preparation of the piperidine compound.

Further object of this invention is to provide a pharmaceutical composition comprising the piperidine compounds as active ingredient.

The piperidine compound of this invention can be represented by the following formula:

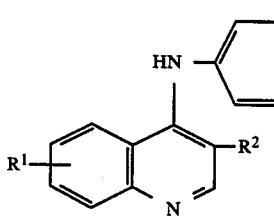

wherein
$R^1$ is hydrogen or trihalomethyl,
$R^2$ is hydrogen or protected carboxy,
$R^3$ is heterocyclic group or aryl which may be halogen substituted, and
X is —S—,

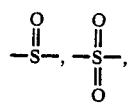

—O—, —NH— or lower alkylene which may be hydroxy substituted,
and pharmaceutically acceptable salts thereof.

Suitable pharmaceutically acceptable salts of the piperidine compound (I) are inorganic or organic acid addition salts such as hydrochloride, hydrobromide, sulfate, nitrate, acetate, p-toluenesulfonate and the like.

According to this invention, the new piperidine compound (I) and pharmaceutically acceptable salts thereof can be prepared by, for example, the following processes.

Process 1:

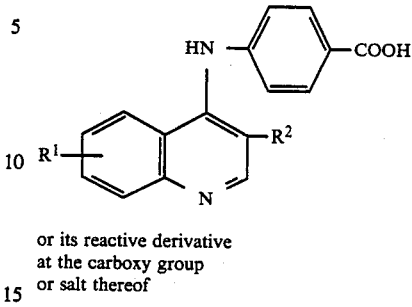

or its reactive derivative at the carboxy group or salt thereof

+

or its reactive derivative at the amino group or salt thereof

↓

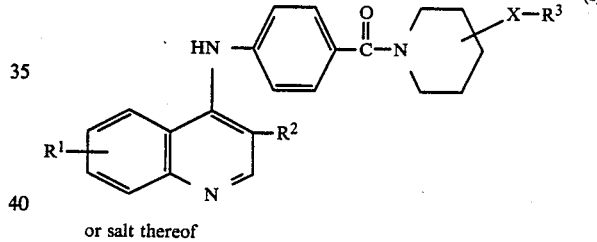

or salt thereof

Process 2:

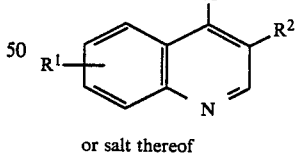

or salt thereof

+

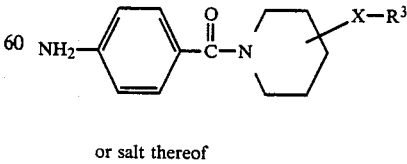

or salt thereof

↓

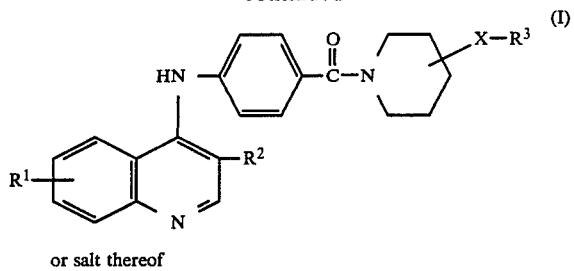

or salt thereof wherein

R[1], R[2], R[3] and X are each as defined above and

A is an acid residue.

In the above and subsequent descriptions of this specification, suitable examples and illustrations of the various definitions are explained in detail in the followings.

The term "lower" is intended to mean 1 to 6 carbon atom(s), unless otherwise indicated.

"Trihalomethyl" may include trifluoromethyl, trichloromethyl, tribromomethyl, triiodomethyl and the like.

"Protected carboxy" may include esterified carboxy such as lower alkoxycarbonyl (e.g. methoxycarbonyl, ethoxycarbonyl, propoxycarbonyl, isopropoxycarbonyl, butoxycarbonyl, isobutoxycarbonyl, t-butoxycarbonyl, pentyloxycarbonyl, hexyloxycarbonyl) and the like.

"Heterocyclic group" may include saturated or unsaturated, monocyclic or polycyclic heterocyclic group containing at least one hetero-atom such as an oxygen, sulfur, nitrogen atom and preferred "heterocyclic group" may be 5 or 6-membered heteromonocyclic group containing nitrogen or sulfur atom such as pyridyl, thienyl and the like.

"Aryl" may include phenyl, tolyl, naphthyl and the like.

"Halogen" may include fluorine, chlorine, bromine, iodine and the like.

"Lower alkylene" may include methylene, ethylene, trimethylene and the like.

"Acid residue" may include halogen (e.g. chlorine, bromine, iodine, fluorine, etc.) and the like.

Suitable salts of the starting compound (II) or its reactive derivative at the carboxy group may include an acid addition salt mentioned above and a salt with a base such as sodium salt, potassium salt, triethylamine salt and the like.

Suitable salts of the starting compound (III), (IV) and (V) may include inorganic or organic acid addition salt mentioned above.

Preferred embodiments of the object compound (I) are as follows.

A preferred embodiment of R[1] is trihalomethyl (more preferably trifluoromethyl); R[2] is hydrogen or protected carboxy [more preferably esterified carboxy (most preferably lower alkoxycarbonyl)]; R[3] is 5 or 6-membered heteromonocyclic group containing nitrogen or sulfur atom (more preferably pyridyl or thienyl) or aryl which may be halogen substituted (more preferably phenyl which may have halogen); X is —S—,

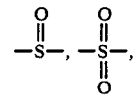

—O—, —NH— or lower alkylene which may be hydroxy substituted.

The processes as illustrated above are explained in more detail by the followings.

PROCESS 1

The object compound (I) or salt thereof can be prepared by reacting the compound (II) or its reactive derivative at the carboxy group or salt thereof with the compound (III) or its reactive derivative at the amino group or salt thereof.

The starting compound (II) includes novel and known ones. For example, 4-[[7-(trifluoromethyl)-4-quinolyl]amino]benzoic acid and preparation thereof are disclosed in Japan Kokai No. 18479/75 corresponding to Chemical Abstracts, volume 84, (1976), 59570y and novel compounds among the starting compound (II) can be prepared in a manner similar thereto.

The starting compound (III) includes novel and known ones. For example, 4-[(4-fluorophenyl)amino]piperidine and preparation thereof are disclosed in U.S. Pat. No. 3,691,176 (1982) and some of novel compounds among the starting compound (III) can be prepared in a manner described in Examples as set forth below. The other compounds can be prepared in a manner similar thereto.

The reactive derivative at the carboxy of the compound (II) may include acid halide (e.g. acid chloride, acid bromide, etc.), acid anhydride, acid azide, activated amide or activated ester (e.g. succinimide ester, etc.), and the like.

The reactive derivative at the amino group of the compound (III) may include a silyl derivative formed by the reaction of the compound (III) with a silyl compound (e.g. bis(trimethylsilyl)acetamide, trimethylsilylacetamide, etc.) and the like.

The reaction can preferably be conducted in the presence of an organic or inorganic base such as alkali or alkaline earth metal hydroxide (e.g. sodium hydroxide, potassium hydroxide, calcium hydroxide, etc.), alkali or alkaline earth metal carbonate or bicarbonate (e.g. sodium carbonate, potassium carbonate, sodium bicarbonate), alkali or alkaline earth metal alkoxide (e.g. sodium ethoxide, lithium methoxide, magnesium methoxide), trialkylamine (e.g. triethylamine), pyridine, bicyclodiaza compound (e.g. 1,5-diazabicyclo[3,4,0]nonene-5,1,5-diazabicyclo[5,4,0]undecene-5, etc.) and the like.

When the starting compound (II) is used in a form of a free acid, the reaction of this process may preferably be conducted in the presence of a condensing agent such as carbodiimidic compound (e.g. N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.), N,N'-carbonyldiimidazole, N,N'-carbonyldi(2-methylimidazole), pentamethyleneketene-N-cyclohexylimine, diphenylketene-N-cyclohexylimine, alkoxyacetylene, 1-alkoxy-1-chloroethylene, trialkylphosphite, ethyl polyphosphate, isopropyl polyphosphate, phosphorus compound (e.g.

phosphorus oxychloride, phosphorus trichloride, etc.), thionyl chloride, oxalyl chloride, 2-ethyl-7-hydroxybenzisoxazolium salt, 2,2,4,4,6,6-hexachloro-1,3,5,2,4,6-triazatriphosphorine, 1-benzenesulphonyloxy-6-chloro-1H-benzotriazole, p-toluenesulfonyl chloride, isopropoxybenzenesulfonyl chloride, or a mixed condensing agent such as triphenylphosphine and a carbon tetrahalide (e.g. carbon tetrachloride, carbon tetrabromide, etc.) or so-called Vilsmeier reagent (e.g. a complex of N,N-dimethylformamide with phosphoryl chloride, phosgene or thionyl chloride, etc.), and the like.

The reaction is usually conducted in a conventional solvent which does not adversely influence the reaction such as water, acetone, dioxane, acetonitrile, ethyl acetate, N,N-dimethylformamide, dimethylsulfoxide, tetrahydrofuran, methylene chloride, chloroform, pyridine, N-methylmorpholine, N-methylpyrrolidine, etc. or a mixture thereof.

The reaction temperature is not critical and this reaction can be conducted at, below or above ambient temperatures.

PROCESS 2

The compound (I) or salt thereof can be prepared by reacting the compound (IV) or salt thereof with the compound (V) or salt thereof.

The compound (V) includes novel and known ones. The detailed method for preparing a novel compound, 1-(4-aminobenzoyl)-4-[(4-fluorophenyl)hydroxymethyl]piperidine is disclosed in Example 8 (1)–(3) as set forth below and novel compounds among the starting compound (V) can be prepared in a manner similar thereto or in a conventional manner.

The reaction is usually conducted in a conventional solvent which does not adversely influence the reaction such as water, methanol, ethanol, propanol, acetone, dioxane, acetonitrile, ethyl acetate, N,N-dimethylformamide, dimethylsulfoxide, tetrahydrofuran, dichloromethane, chloroform, pyridine, N-methylmorpholine, N-methylpyrrolidine, etc. or a mixture thereof.

The reaction temperature is not critical and this reaction can be conducted at, below or above ambient temperatures.

The object compound (I) thus obtained can be purified, isolated from the reaction mixture and converted to the desired salts in a conventional manner.

The piperidine compound (I) has excellent antihypertensive activity and less side effects (e.g. diarrhea, decreasing of sperm motility, gastric lesion, etc.) and therefore is useful as an antihypertensive agent.

The following Tests illustrate the antihypertensive activity of compound (I).

TEST (a) Test method:

Five-week old male Wister rats were uninephrectomized under anesthesia. Deoxycorticosterone acetate (DOCA) (30 mg/kg), suspended in peanut oil, was injected subcutaneously twice a week and 1% saline was substituted for the drinking water. Animals with mean blood pressure 150–200 mmHg were used for experiment between 5 and 7 weeks after surgery.

The test compounds (Dosage: 10 mg/kg) were administered orally to the test animals.

Blood pressure was measured at the femoral artery by means of a pressure transducer and recorded as electrically integrated values of mean arterial pressure.

(b) Test compound:
A formula of the compound:

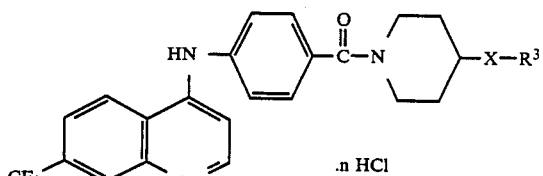

| Test compound No. | X | $R^3$ | n |
|---|---|---|---|
| 1 | —S— | 4-F-phenyl | 0 |
| 2 | —S(=O)— | 4-F-phenyl | 0 |
| 3 | —S(=O)$_2$— | 4-F-phenyl | 1 |
| 4 | —S— | 2-F-phenyl | 0 |
| 5 | —S(=O)$_2$— | 2-F-phenyl | 1 |
| 6 | —S— | 2-pyridyl | 2 |
| 7 | —CH$_2$— | phenyl | 1 |
| 8 | —CH(OH)— | 4-F-phenyl | 1 |
| 9 | —O— | 4-F-phenyl | 1 |
| 10 | —NH— | 4-F-phenyl | 2 |

(c) Test results:

The results are shown in the following Table.

| Test compound No. | Maximum decrease of blood pressure (%) |
| --- | --- |
| 1 | 37 |
| 2 | 35 |
| 3 | 44 |
| 4 | 34 |
| 5 | 37 |
| 6 | 51 |
| 7 | 32 |
| 8 | 44 |
| 9 | 44 |
| 10 | 50 |

The piperidine compound (I) can be used as an antihypertensive agent either in free form or in the form of the pharmaceutically acceptable salts such as an acid addition salt (e.g. hydrochloride, sulfate, acetate, p-toluenesulfonate).

Compound (I) or its pharmaceutically acceptable salt can usually be administered to mammals including human beings in the form of a conventional pharmaceutical composition such as capsule, microcapsule, tablet, granule, powder, troche, syrup, aerosol, micronized powder, inhalation, solution, injection, suspension, emulsion, suppository, ointment, or the like.

The pharmaceutical composition of this invention can contain various organic or inorganic carrier materials, which are conventionally used for pharmaceutical purposes, such as excipient (e.g. sucrose, starch, mannit, sorbit, lactose, glucose, cellulose, talc, calcium phosphate, calcium carbonate, etc.), binding agent (cellulose, methyl cellulose, hydroxypropylcellulose, polypropylpyrrolidone, gelatin, gum arabic, polyethyleneglycol, sucrose, starch, etc.), disintegrator (e.g. starch, carboxymethyl cellulose, calcium salt of carboxymethyl cellulose, hydroxypropylstarch, sodium glycole-starch, sodium bicarbonate, calcium phosphate, calcium citrate, etc.), lubricant (e.g. magnesium stearate, aerosil, talc, sodium laurylsulfate, etc.), flavoring agent (e.g. citric acid, mentol, glycine, orange powders, etc.), preservative (sodium benzoate, sodium bisulfite, methylparaben, propylparaben, etc.) stabilizer (citric acid, sodium citrate, acetic acid, etc.), suspending agent (e.g. methyl cellulose, polyvinylpyrrolidone, aluminum stearate, etc.), dispersing agent, aqueous diluting agent (e.g. water), base wax (e.g. cacao butter, polyethyleneglycol, white petrolatum, etc.).

The dosage of the present active ingredient is to be varied depending on various factors such as weight and/or age of a patient and/or a stage of the allergic disease, and further the route of administration chosen. In general, the optimum dosage of compound (I) or its pharmaceutically acceptable salt to human body can be selected within a range of 0.1–100 mg/kg.

The following Examples are given for the purpose of illustrating this invention.

EXAMPLE 1

(1) A mixture of 4-chloro-1-methylpiperidine (110.1 g), 2-fluorothiophenol (117.3 g), and potassium carbonate (170.8 g) in N,N-dimethylformamide (1.0 l) was stirred at 90° C. for 2 hours and filtered. The filtrate was concentrated in vacuo to give an oily residue, which was diluted with brine and extracted three times with diethyl ether. The extracts were dried over magnesium sulfate, concentrated in vacuo, and distilled to give 4-[(2-fluorophenyl)thio]-1-methylpiperidine (111.1 g) as a yellow oil.

bp: 119°–123° C./0.4 mmHg.

IR (film): 3060, 2930, 2840, 2780, 2720, 2670 cm$^{-1}$.

NMR (CDCl$_3$, δ): 1.3–2.2 (6H, m), 2.25 (3H, s), 2.65–3.35 (3H, m), 6.85–7.65 (4H, m).

(2) A solution of phenyl chlorocarbonate (91.4 g) in dry methylene chloride (269 ml) was added dropwise to a stirred solution of 4-[(2-fluorophenyl)thio]-1-methylpiperidine (107.6 g) in dry methylene chloride (538 ml) under ice-cooling over a period of 1.5 hours. The resultant solution was stirred under ice-cooling for 30 minutes and at room temperature for 1.5 hours, then diluted with 1N hydrochloride acid. The methylene chloride layer was separated, washed with 5% sodium hydroxide solution and brine, dried over magnesium sulfate, and chromatographed on silica gel using methylene chloride as an eluent to give a yellow oil (133.9 g). The oil (0.49 g) was crystallized from n-hexane to give phenyl 4-[(2-fluorophenyl)thio]-1-piperidine carboxylate (0.25 g) as colourless powder.

mp: 58°–60° C.

IR (Nujol): 1730, 1710 cm$^{-1}$.

NMR (CDCl$_3$, δ): 1.3–2.25 (4H, m), 2.85–3.75 (3H, m), 3.9–4.35 (2H, m), 6.9–7.65 (9H, m).

(3) 3-Chloroperbenzoic acid (73.2 g) was slowly added to a stirred solution of phenyl 4-[(2-fluorophenyl)thio]-1-piperidine-carboxylate (122.2 g) in chloroform (1.10 l) under ice-cooling over a period of 25 minutes and the mixture was stirred at the same temperature for 1 hour. Additional 3-chloroperbenzoic acid (66.9 g) was slowly added with stirring at the same temperature over a period of 15 minutes. The resultant mixture was stirred at room temperature for 1 hour and then filtered. The filtrate was washed successively with sodium bisulfite solution, sodium bicarbonate solution, and brine, dried over magnesium sulfate and concentrated to dryness in vacuo. The solid residue was recrystallized from a mixture of diisopropyl ether and ethyl acetate to give phenyl 4-[(2-fluorophenyl)sulfonyl]-1-piperidine-carboxylate (102.2 g) as colourless powder.

mp: 160°–161° C.

IR (Nujol): 1740, 1720, 1330, 1150 cm$^{-1}$.

NMR (CDCl$_3$, δ): 1.7–2.3 (4H, m), 2.75–3.75 (3H, m), 4.25–4.5 (2H, m), 7.0–8.15 (9H, m).

(4) A mixture of phenyl 4-[(2-fluorophenyl)sulfonyl]-1-piperidine-carboxylate (97.0 g) and 47% hydrobromic acid (1.11 l) was stirred under reflux for 1 hour and concentrated in vacuo. The residue was suspended in water (700 ml). The suspension was adjusted to alkaline pH with 20% sodium hydroxide solution (370 ml) and then extracted twice with methylene chloride. The extracts were combined and dried over magnesium sulfate. After removal of magnesium sulfate, the solution was treated with methanolic hydrochloric acid and concentrated to dryness in vacuo. The powdery residue was washed with ethanol and diethyl ether to give 4-[(2-fluorophenyl)sulfonyl]piperidine hydrochloride (67.85 g) as colorless powder.

mp: 264°–265° C.

IR (Nujol): 2800–2300, 1340, 1320, 1150 cm$^{-1}$.

NMR (DMSO-d$_6$, δ): 1.65–2.35 (4H, m), 2.65–4.0 (5H, m), 7.35–8.1 (4H, m), 9.4 (2H, broad s).

(B 5) 4-[[7-(Trifluoromethyl)-4-quinolyl]amino]benzoyl chloride hydrochloride (65.20 g) was added slowly to a stirred mixture of 4-[(2-fluorophenyl)sulfonyl]piperidine hydrochloride (47.0 g) and triethylamine (117.2 ml) in dry methylene chloride (1.01 l) at room temperature. The resultant mixture was stirred at the same temperature for 1 hour and under ice cooling for 0.5 hours. The precipitated powder was collected by filtration, washed with a mixture of methylene chloride and water, and suspended in a mixture of chloroform and methanol. Excess methanolic hydrochloric acid was added to the suspension and the resulting solution was concentrated in vacuo to give an oil. The oil was triturated in a mixture of ethyl acetate and ethanol to give powdery 4-[(2-fluorophenyl)sulfonyl]-1-[4-[[7-(trifluoromethyl)-4-quinolyl]amino]benzoyl]piperidine hydrochloride (46.73 g).

(1) The object compound recrystallized from ethanol

IR (Nujol): 3220-3040 (m), 2500 (broad), 1610, 1590, 1320, 1150 cm$^{-1}$.

NMR (DMSO-d$_6$, δ): 1.45-2.2 (4H, m), 2.8-4.6 (5H, m), 7.07 (1H, d, J=7 Hz), 7.4-8.25 (9H, m), 8.63 (1H, broad s), 8.67 (1H, d, J=7 Hz), 9.30 (1H, broad d, J=9 Hz), 11.6 (1H, broad).

X ray diffraction (Target, Cu; Filter, Ni; Voltage, 30 KV; Current, 10 m A; Time constant, 0.5 second; Scanning speed, 2°/minute; Chart speed, 2 cm/minute; Divergence slit, 1°; Receiving slit, 0.15 m m; Scatter slit, 1°):

(2) The object compound recrystallized from a mixture of water and ethanol

NMR values are the same as those of the above (1).

IR (Nujol): 3500-3040 (m), 2800-2300 (m), 1640, 1620 (shoulder), 1595, 1560, 1325, 1135 cm$^{-1}$.

X ray diffraction [Analysis condition is the same as that of the above (1)]:

|  | peak No. | | | | | | | | | |
| --- | --- | --- | --- | --- | --- | --- | --- | --- | --- | --- |
|  | 1 | 2 | 3 | 4 | 5 | 6 | 7 | 8 | 9 | 10 |
| 2θ (Bragg diffraction angle) | 9.6° | 11.6° | 12.1° | 12.8° | 13.6° | 15.6° | 17.1° | 18.6° | 19.3° | 19.7° |
| I/Io (relative intensity) | 40 | 42 | 31 | 36 | 47 | 37 | 93 | 23 | 100 | 72 |
|  | peak No. | | | | | | | | | |
|  | 11 | 12 | 13 | 14 | 15 | 16 | 17 | 18 | 19 | 20 |
| 2θ (Bragg diffraction angle) | 20.4° | 20.9° | 21.4° | 22.2° | 22.9° | 24.4° | 25.6° | 27.4° | 28.2° | 29.0° |
| I/Io (relative intensity) | 45 | 44 | 24 | 70 | 58 | 48 | 92 | 21 | 38 | 33 |

Thermal analysis [Analysis condition is the same as that of the above (1)]:

Dehydration (69° C.)→melt (201° C.)→decomposition (304° C.).

(3) The object compound recrystallized from a mixture of methanol and ethyl acetate NMR values are the same as those of the ablve (1).

IR (Nujol): 3600-3050 (m), 2800-2350 (m), 1640, 1620, 1595, 1560, 1325, 1135 cm$^{-1}$.

X ray diffraction [Analysis condition is the same as that of the above (1)]:

|  | peak No. | | | | | | | | | | | | | | |
| --- | --- | --- | --- | --- | --- | --- | --- | --- | --- | --- | --- | --- | --- | --- | --- |
|  | 1 | 2 | 3 | 4 | 5 | 6 | 7 | 8 | 9 | 10 | 11 | 12 | 13 | 14 | 15 |
| 2θ (Bragg diffraction angle) | 9.3° | 11.7° | 13.6° | 15.9° | 16.9° | 18.8° | 20.9° | 21.8° | 22.3° | 22.9° | 23.4° | 24.2° | 25.3° | 27.9° | 29.2° |
| I/Io (relation intensity) | 36 | 27 | 27 | 53 | 23 | 100 | 26 | 42 | 38 | 30 | 39 | 28 | 55 | 21 | 23 |

Thermal analysis [Analysis condition is the same as that of the above (1)]:

Melt (197° C.)→decomposition (308° C.).

(4) The object compound recrystallized from a mixture of ethanol and dioxane

NMR values are the same as those of the above (1).

|  | peak No. | | | | | | | | | | |
| --- | --- | --- | --- | --- | --- | --- | --- | --- | --- | --- | --- |
|  | 1 | 2 | 3 | 4 | 5 | 6 | 7 | 8 | 9 | 10 | 11 |
| 2θ (Bragg diffraction angle) | 8.3° | 13.9° | 15.6° | 16.6° | 17.4° | 18.5° | 18.9° | 19.3° | 20.1° | 21.0° | 21.4° |
| I/Io (relative intensity) | 38 | 23 | 35 | 100 | 29 | 43 | 38 | 33 | 37 | 41 | 48 |
|  | peak No. | | | | | | | | | | |
|  | 12 | 13 | 14 | 15 | 16 | 17 | 18 | 19 | 20 | 21 | |
| 2θ (Bragg diffraction angle) | 22.2° | 23.0° | 25.0° | 25.6° | 26.4° | 26.7° | 27.1° | 27.7° | 28.8° | 29.6° | |
| I/Io (relative intensity) | 61 | 21 | 35 | 28 | 41 | 42 | 44 | 27 | 17 | 24 | |

Thermal analysis [Atmosphere, N$_2$ (30 ml/minute); Sensitivity, DTA: ±250μ V, TG: ±5 mg; Heating rate, 10° C./minute]:
Melt (225° C.)→decomposition (306° C.).

IR (Nujol): 3250-3010 (m), 2800-2200 (m), 1655 (shoulder), 1615, 1595, 1320, 1165, 1145, 1130 cm$^{-1}$.

X ray diffraction [Analysis condition is the same as that of the above (1)]:

|  | peak No. | | | | | | | | | | | | | | |
| --- | --- | --- | --- | --- | --- | --- | --- | --- | --- | --- | --- | --- | --- | --- | --- |
|  | 1 | 2 | 3 | 4 | 5 | 6 | 7 | 8 | 9 | 10 | 11 | 12 | 13 | 14 | 15 |
| 2θ (Bragg diffraction angle) | 8.6° | 10.5° | 11.8° | 12.8° | 14.5° | 14.8° | 15.8° | 16.5° | 17.8° | 18.4° | 18.9° | 19.3° | 20.2° | 20.7° | 21.2° |
| I/Io (relation intensity) | 12 | 47 | 27 | 18 | 44 | 44 | 15 | 28 | 22 | 45 | 25 | 19 | 100 | 24 | 47 |
|  | peak No. | | | | | | | | | | | | | | |
|  | 16 | 17 | 18 | 19 | 20 | 21 | 22 | 23 | 24 | 25 | 26 | 27 | 28 | 29 | |
| 2θ (Bragg diffraction angle) | 21.6° | 22.0° | 22.2° | 22.9° | 23.3° | 23.7° | 24.0° | 24.3° | 25.2° | 25.7° | 26.7° | 27.2° | 28.3° | 29.6° | |

| I/Io (relation intensity) | 21 | 34 | 20 | 42 | 31 | 28 | 22 | 15 | 22 | 24 | 21 | 16 | 15 | 15 |
|---|---|---|---|---|---|---|---|---|---|---|---|---|---|---|

Thermal analysis [Analysis condition is the same as that of the above (1)]:
Endothermic change (193° C.)→exothermic change

EXAMPLE 2

(1) The following compound was prepared in a similar manner to that of Example 1 (2).
Phenyl 4-[(4-fluorophenyl)thio]-1-piperidinecarboxylate.
mp: 64°–66° C.
IR (Nujol): 1720 cm$^{-1}$.
NMR (CDCl$_3$, δ): 1.25–2.25 (4H, m), 2.9–3.45 (3H, m), 3.95–4.4 (2H, m), 6.85–7.6 (9H, m).

(2) The following compound was prepared in a similar manner to that of Example 1 (4).
4-[(4-Fluorophenyl)thio]piperidine hydrochloride.
mp: 170°–173° C. (recrystallized from a mixture of ethyl acetate and isopropanol).
IR (Nujol): 2800, 2720, 2670, 2560, 2460 cm$^{-1}$.
NMR (DMSO-d$_6$, δ): 1.4–2.3 (4H, m), 2.7–3.7 (5H, m), 7.05–7.7 (4H, m), 9.4 (2H, broad s).

(3) 4-[[7-(Trifluoromethyl)-4-quinolyl]amino]benzoyl chloride hydrochloride (0.94 g) was added slowly to a stirred mixture of 4-[(4-fluorophenyl)thio]piperidine hydrochloride (0.60 g) and triethylamine (1.69 ml) in dry methylene chloride (12.5 ml) at room temperature. The resultant mixture was stirred at the same temperature for 3.5 hours. The precipitated powder was collected by filtration and washed with methylene chloride and diethyl ether to give 4-[(4-fluorophenyl)thio]-1-[4-[[7-(trifluoromethyl)-4-quinolyl]amino]benzoyl]piperidine (0.45 g) as colourless powder.
mp: 211°–214° C.
IR (Nujol): 3300, 1610 cm$^{-1}$.
NMR (DMSO-d$_6$, δ): 1.05–2.15 (4H, m), 2.85–4.3 (5H, m), 7.0–8.75 (13H, m), 9.35 (1H, broad s).

EXAMPLE 3

(1) 3-Chloroperbenzoic acid (0.96 g) was slowly added to a stirred solution of 4-[(4-fluorophenyl)thio]piperidine hydrochloride (I.2g) in chloroform (60 ml) under ice-cooling over a period of 5 minutes and the mixture was stirred at the same temperature for 45 minutes. After being treated with sodium bisulfite solution under ice-cooling, the resultant mixture was adjusted to alkaline pH with 20% sodium hydroxide solution. The chloroform layer was separated and the aqueous layer was extracted three times with chloroform. The chloroform layers were combined and dried over magnesium sulfate. After removal of magnesium sulfate, the solution was treated with ethereal hydrochloric acid and concentrated to dryness in vacuo. The powdery residue was washed with isopropanol to give 4-[(4-fluorophenyl)sulfinyl]piperidine hydrochloride (1.10 g) as colourless powser.
mp: 208°–210° C.
IR (Nujol): 2730, 2680, 2580, 2460, 1040 cm$^{-1}$.
NMR (DMSO-d$_6$, δ): 1.5–2.1 (4H, m), 2.7–3.5 (5H, m), 7.4–8.05 (4H, m), 9.5 (2H, broad).

(2) 4-[[7-(Trifluoromethyl)-4-quinolyl]amino]benzoyl chloride hydrochloride (14.7 g) was added slowly to a stirred mixture of 4-[(4-fluorophenyl)sulfinyl]piperidine hydrochloride (10.0 g) and triethylamine (26.4 ml) in dry methylene chloride (440 ml) at room temperature. The resultant mixture was stirred at the same temperature for 3 hours, and concentrated to dryness in vacuo. Water was added to the residue and the precipitated powder was collected by filtration, washed with water, and dried to give a powder. The powder was washed with methylene chloride to give 4-[(4-fluorophenyl)sulfinyl]-1-[4-[[7-(trifluoromethyl)-4-quinolyl]amino]benzoyl]piperidine (13.60 g) as colourless powder.
mp: 215°–216.5° C.
IR (Nujol): 3320, 1615, 1565, 1040 cm$^{-1}$.
NMR (CDCl$_3$-CD$_3$OD, δ): 1.5–2.15 (4H, m), 2.65–3.15 (3H, m), 4.15–4.5 (2H, m), 7.1–8.65 (13H, m).

EXAMPLE 4

(1) A solution of phenyl chlorocarbonate (17.3 g) in dry methylene chloride (40 ml) was dropwise added to a stirred solution of 4-chloro-1-methylpiperidine (13.3 g) in dry methylene chloride (60 ml) under ice-cooling over a period of 5 minutes. The resultant mixture was stirred at the same temperature for 30 minutes and then at room temperature for 6 hours. The mixture was washed with water, dried over magnesium sulfate, and concentrated in vacuo to give an oil, which was distilled to give phenyl 4-chloro-1-piperidine-carboxylate (17.0 g) as a colourless oil.
bp: 144°–148° C./0.5 mmHg.
IR (film): 1730 cm$^{-1}$.
NMR (CCl$_4$, δ): 1.5–2.3 (4H, m), 3.2–4.3 (5H, m), 7.0–7.6 (5H, m).

(2) 60% Sodium hydride dispersion in a mineral oil (2.40 g) was slowly added to an ice-cooled solution of phenyl 4-chloro-1-piperidine-carboxylate (15.2 g) and 4-mercaptopyridine (6.66 g) in dry N,N-dimethylformamide (150 ml) with stirring under nitrogen gas. The mixture was stirred at the same temperature for 30 minutes and then at 80° C. for 4.5 hours. The resultant reaction mixture was poured into ice-water and extracted with diethyl ether. The extract was washed with water, dried over magnesium sulfate, and concentrated to dryness in vacuo. The crystalline residue was recrystallized from a mixture of n-hexane and isopropanol to give phenyl 4-[(4-pyridyl)thio]-1-piperidine-carboxylate (15.4 g) as colourless crystals.
mp: 102°–104° C.
IR (Nujol): 1725 cm$^{-1}$.
NMR (CDCl$_3$, δ): 1.7–2.4 (4H, m), 3.0–3.8 (3H, m), 4.0–4.3 (2H, m), 7.0–8.5 (9H, m).

(3) A solution of phenyl 4-[(4-pyridyl)thio]-1-piperidine-carboxylate (5.0 g) in conc. hydrochloric acid (50 ml) was refluxed for 7 hours and concentrated to dryness in vacuo. The crystalline residue was washed with isopropanol and recrystallized from methanol to give 4-[(4-pyridyl)thio]piperidine dihydrochloride (2.85 g).
mp: 275°–282° C.
IR (Nujol): 2850–1800 cm$^{-1}$.
NMR (D$_2$O, δ): 1.8–2.7 (4H, m), 3.0–3.8 (4H, m), 4.13 (1H, m), 7.90 (2H, dd, J=7 Hz), 8.50 (2H, dd, J=7 Hz).

(4) 4-[[7-(Trifluoromethyl)-4-quinolyl]amino]benzoyl chloride hydrochloride (1.88 g) was added slowly to a stirred mixture of 4-[(4-pyridyl)thio]piperidine dihydrochloride (1.30 g) and triethylamine (2.92 g) in dry methylene chloride (60 ml) at room temperature. The resultant mixture was stirred at the same temperature for 6 hours and concentrated to dryness in vacuo to give a solid, which was triturated in water and filtered to give light yellow crystals (2.56 g). The crystals (2.0 g) was dissolved in a mixture of chloroform and ethanol and excess ethanolic hydrochloric acid was added to the solution. The resultant solution was concentrated to dryness in vacuo to give crystals, which were washed with isopropanol and recrystallized from ethanol to give 4-[(4-pyridyl)thio]-1-[4-[[7-(trifluoromethyl)-4-quinolyl]amino]benzoyl]piperidine dihydrochloride (1.26 g) as pale yellow crystals.
mp: 221°-225° C.
IR (Nujol): 2560, 1620, 1590 cm$^{-1}$.
NMR (DMSO-d$_6$, δ): 1.6-2.2 (4H, m), 3.0-4.3 (5H, m), 7.0-9.4 (13H, m).

EXAMPLE 5

(1) 30% Hydrogen peroxide (10 ml) was added dropwise to a stirred solution of 4-[(4-pyridyl)thio]piperidine dihydrochloride (2.0 g) in acetic acid (30 ml) at room temperature over a period of 20 minutes and the mixture was stirred at the same temperature for 40 minutes. Then the mixture was stirred at 70° C. for 8 hours and additional 30% Hydrogen peroxide (10 ml) was added. The resultant mixture was stirred at 70° C. for 1 hour, treated with excess sodium sulfite under ice-cooling, and concentrated in vacuo. The residue was dissolved in water. The solution was adjusted to alkaline pH with 5N aqueous potassium hydroxide and extracted several times with chloroform. The extracts were collected, dried over magnesium sulfate, and concentrated to dryness in vacuo. The crystalline residue was recrystallized from isopropanol to give 4-[(4-pyridyl)sulfonyl]piperidine (0.87 g).
mp: 88°-91° C.
IR (Nujol): 3300, 3200, 1320, 1150 cm$^{-1}$.
NMR (CDCl$_3$, δ): 1.5-3.5 (10H, m), 7.8-9.0 (4H, m).

(2) 4-[[7-(Trifluoromethyl)-4-quinolyl]amino]benzoyl chloride hydrochloride (0.90 g) was added slowly to a stirred mixture of 4-[(4-pyridyl)sulfonyl]piperidine (0.50 g) and triethylamine (0.70 g) in dry methylene chloride (40 ml) at room temperature. The resultant mixture was stirred at the same temperature for 3.5 hours and the precipitated crystals were collected by filtration. The filtrate was washed with water, dried over magnesium sulfate, and concentrated to dryness in vacuo to give a crystalline residue, which was washed with isopropanol. The obtained crystals were combined and those dihydrochloride was obtained by treating with excess ethanolic hydrochloric acid. The dihydrochloride was recrystallized from a mixture of isopropanol and methanol to give 4-[(4-pyridyl)sulfonyl]-1-[4-[[7-(trifluoromethyl)-4-quinolyl]amino]benzoyl]piperidine dihydrochloride (0.73 g).
mp: 190°-194° C.
IR (Nujol): 1620, 1600, 1325, 1155, 1130 cm$^{-1}$.
NMR (DMSO-d$_6$, δ): 1.4-2.1 (4H, m), 2.6-4.2 (5H, m), 7.0-9.2 (13H, m), 11.67 (1H, s).

EXAMPLE 6

(1) The following compound was prepared in a similar manner to that of Example 4 (2).
Phenyl 4-[(2-pyridyl)thio]-1-piperidine-carboxylate.
mp: 92°-94° C.
IR (Nujol): 1720 cm$^{-1}$.
NMR (DMSO-d$_6$, δ): 1.35-2.5 (4H, m), 3.1-3.85 (3H, m), 3.85-4.5 (2H, m), 7.0-7.85 (8H, m), 8.35-8.65 (1H, m).

(2) The following compound was prepared in a similar manner to that of Example 4 (3).
4-[(2-Pyridyl)thio]piperidine dihydrochloride.
mp: 228°-235° C.
IR (Nujol): 2800-2100 cm$^{-1}$.
NMR (D$_2$O, δ): 1.7-2.7 (4H, m), 3.25-4.5 (5H, m), 7.7-8.85 (4H, m).

(3) m-Chloroperbenzoic acid (0.77 g) was added to an ice-cooled solution of 4-[(2-pyridyl)thio]piperidine dihydrochloride (1.0 g) in water (20 ml) and the mixture was stirred at the same temperature for 7.5 hours. After additional m-chloroperbenzoic acid (0.07 g) and water (5 ml) were added, the mixture was stirred at the same temperature for 1 hour, adjusted to alkaline pH with sodium hydroxide solution, and extracted several times with chloroform. The extracts were combined, dried over magnesium sulfate, and concentrated in vacuo. The oily residue was dissolved in chloroform. The solution was treated with ethanolic hydrochloric acid and concentrated in vacuo. The crystalline residue was washed with isopropanol to give 4-[(2-pyridyl)sulfinyl]piperidine hydrochloride (0.70 g).
mp: 213.5°-215° C.
IR (Nujol): 2750-2400, 1040 cm$^{-1}$.
NMR (D$_2$O, δ): 1.35-2.8 (4H, m), 2.8-3.9 (5H, m), 7.55-8.35 (3H, m), 8.65-9.0 (1H, m).

(4) 4-[[7-(Trifluoromethyl)-4-quinolyl]amino]benzoyl chloride hydrochloride (0.69 g) was added slowly to a stirred mixture of 4-[(2-pyridyl)sulfinyl]piperidine hydrochloride (0.50 g) and triethylamine (1.72 ml) in dry methylene chloride (22 ml) at room temperature. The resultant mixture was stirred at the same temperature for 1.5 hours and concentrated in vacuo. The residue was partitioned between chloroform and water. The organic layer was washed with saturated aqueous sodium bicarbonate, dried over magnesium sulfate, and concentrated to dryness in vacuo. The resultant crystalline residue was recrystallized from a mixture of methylene chloride and methanol and washed successively with methanol and methylene chloride to give 4-[(2-pyridyl(sulfinyl]-1-[4-[[7-(trifluoromethyl)-4-quinolyl]amino]benzoyl]piperidine (0.59 g).
mp: 214°-215.5° C.
IR (Nujol): 3325, 1610, 1565, 1040 cm$^{-1}$.
NMR (CDCl$_3$-CD$_3$OD, δ): 1.0-2.5 (4H, m), 2.5-3.65 (3H, m), 3.85-4.4 (2H, m), 7.0-8.8 (13H, m).

EXAMPLE 7

4-[[7-Trifluoromethyl)-4-quinolyl]amino]benzoyl chloride hydrochloride (1.0 g) was added slowly to a stirred mixture of 4-benzylpiperidine (0.45 g) and triethylamine (0.78 g) in dry methylene chloride (17 ml) at room temperature. The resultant mixture was stirred at the same temperature for 2 hours and diluted with an aqueous sodium bicarbonate. The precipitated powder was collected by filtration and the methylene chloride layer was concentrated to dryness in vacuo. The collected powder and the residue were combined, dissolved in ethyl acetate, washed with water, dried over magnesium sulfate, and concentrated to dryness in vacuo. The residue was treated with excess ethanolic hydrochloric acid to give the corresponding hydrochloride, which was triturated in ethyl acetate. The precipitated powder was collected and recrystallized from ethanol to give 4-benzyl-1-[4-[[7-(trifluoromethyl)-4-quinolyl]amino]benzoyl]piperidine hydrochloride (0.51 g).
mp: 240°-242° C.

IR (Nujol): 3200–3020, 2550 (broad), 1635, 1620, 1590 cm$^{-1}$

NMR (DMSO-d$_6$, δ): 0.7–2.0 (5H, m), 2.75–3.2 (2H, m), 3.4–4.35 (4H, m), 6.93 (1H, d, J=7 Hz), 7.13 (5H, s), 7.48 (4H, s), 8.05 (1H, broad d, J=9 Hz), 8.63 (1H, broad s), 8.67 (1H, d, J=7 Hz), 9.15 (1H, broad d, J=9 Hz), 11.3 (1H, broad).

EXAMPLE 8

(1) 4-Nitrobenzoyl chloride (3.08 g) was added slowly to a stirred mixture of 4-(4-fluorobenzoyl)piperidine hydrochloride (4.0 g) and triethylamine (4.98 g) in methylene chloride (110 ml) at room temperature. The resulting mixture was stirred at this temperature for 1 hour, washed with 1N hydrochloric acid, saturated sodium bicarbonate solution, and brine, dried over magnesium sulfate and concentrated in vacuo. The residue was recrystallized from a mixture of acetone and methanol to give 4-(4-fluorobenzoyl)-1-(4-nitrobenzoyl)piperidine (5.0 g) as colourless crystals.

mp: 168.5°–170° C.

IR (Nujol): 1680, 1625, 1515, 1360, 1340 cm$^{-1}$.

NMR (DMSO-d$_6$, δ): 1.2–2.1 (4H, m), 2.85–4.15 (4H, m), 4.15–4.8 (1H, m), 7.2–8.4 (8H, m).

(2) 4-(4-Fluorobenzoyl)-1-(4-nitrobenzoyl)piperidine (4.75 g) was added slowly to a stirred mixture of iron powder (4.75 g), ammonium chloride (0.57 g), water (28.5 ml), ethanol (38 ml) and methyl cellosolve (76 ml) under reflux. The resulting mixture was stirred under reflux for 30 minutes and filtered. The filtrate was concentrated in vacuo. The residue was diluted with saturated sodium bicarbonate solution and extracted twice with methylene chloride. The extract was washed with brine, dried over magnesium sulfate and concentrated in vacuo. The resulting residue was recrystallized from ethanol to give 1-(4-aminobenzoyl)-4-(4-fluorobenzoyl)piperidine (3.6 g) as pale yellow crystals.

mp: 182°–184° C.

IR (Nujol): 3460, 3440, 3320, 3210, 1675, 1635 cm$^{-1}$.

NMR (DMSO-d$_6$, δ): 1.3–2.1 (4H, m), 2.8–3.2 (2H, m), 3.4–3.95 (1H, m), 3.95–4.4 (2H, m), 5.43 (2H, s), 6.55 (2H, d, J=8 Hz), 7.13 (2H, d, J=8 Hz), 7.32 (2H, t, J=9 Hz), 8.07 (2H, m).

(3) Sodium borohydride (0.058 g) was added to a solution of 1-(4-aminobenzoyl)-4-(4-fluorobenzoyl)piperidine (1.0 g) in methanol (80 ml) and the mixture was stirred at room temperature for 2 hours. Additional sodium borohydride (0.050 g) was added. After being stirred at the same temperature for 1.5 hours, the resultant mixture was concentrated in vacuo. The residue was diluted with water and extracted twice with methylene chloride. The extracts were combined, washed with brine, dried over magnesium sulfate, and concentrated to dryness in vacuo. The powdery residue was washed with diisopropyl ether to give 1-(4-aminobenzoyl)-4-[(4-fluorophenyl)hydroxymethyl]piperidine (1.00 g) as pale yellow powder.

mp: 82° C. (dec.).

IR (Nujol): 3350 (broad), 3240, 1605 cm$^{-1}$.

NMR (CDCl$_3$, δ): 1.1–4.5 (13H, m), 6.57 (2H, d, J=9 Hz), 6.8–7.4 (8H, m).

(4) A mixture of 4-chloro-7-(trifluoromethyl)quinoline (0.32 g) and 1-(4-aminobenzoyl)-4-[(4-fluorophenyl)hydroxymethyl]piperidine (0.45 g) in dry ethanol (10 ml) was stirred under reflux for 4 hours and concentrated to dryness in vacuo. The residue was recrystallized from a mixture of ethyl acetate and isopropanol to give 4-[(4-fluorophenyl)hydroxymethyl]-1-[4-[[7-(trifluoromethyl)-4-quinolyl]amino]benzoyl]piperidine hydrochloride (0.65 g) as pale yellow powder.

mp: 218°–223° C.

IR (Nujol): 3350, 3340, 2800–2400, 1620, 1600, 1580 cm$^{-1}$.

NMR (DMSO-d$_6$, δ): 1.0–4.5 (11H, m), 7.0–9.3 (13H, m), 11.5 (1H, broad).

EXAMPLE 9

(1) The following compound was prepared in a similar manner to that of Example 1 (3).

Phenyl 4-[(4-fluorophenyl)sulfonyl]-1-piperidinecarboxylate.

mp: 144°–146° C. (recrystallized from diisopropyl ether-ethyl acetate).

IR (Nujol): 1710, 1320, 1140 cm$^{-1}$

NMR (CDCl$_3$, δ): 1.45–2.2 (4H, m), 2.7–3.3 (3H, m), 4.3–4.55 (2H, m), 7.0–7.5 (7H, m), 7.8–8.05 (2H, m).

MS (m/e): 363 (M$^+$), 270 (base), 159, 143, 95, 77.

(2) The following compound was prepared in a similar manner to that of Example 1 (4).

4-[(4-Fluorophenyl)sulfonyl]piperidine hydrochloride.

mp: 242°–247° C. (recrystallized from a mixture of ethanol and methanol).

IR (Nujol): 2700, 2640, 2490, 1310, 1150 cm$^{-1}$.

NMR (DMSO-d$_6$, δ): 1.6–2.15 (4H, m), 2.7–3.9 (5H, m), 7.35–8.1 (4H, m), 9.35 (2H, broad).

MS (m/e): 244 (M$^+$+1), 243 (M$^+$), 95, 84, 55 (base).

(3) The following compound was prepared in a similar manner to that of Example 1 (5).

4-[(4-fluorophenyl)sulfonyl]-1-[4-[[7-(trifluoromethyl)-4-quinolyl]amino]benzoyl]piperidine hydrochloride.

mp: 199°–204° C. (recrystallized from ethanol).

IR (Nujol): 2650 (broad), 1635, 1610, 1585, 1320, 1140 cm$^{-1}$.

NMR (DMSO-d$_6$, δ): 1.2–2.2 (4H, m), 2.65–4.5 (5H, m), 7.0–9.35 (13H, m), 11.5 (1H, broad).

EXAMPLE 10

(1) A mixture of ethyl 4-chloro-7-(trifluoromethyl)-3-quinoline-carboxylate (3.04 g) and 4-aminobenzoic acid (1.37 g) in tetrahydrofuran (53 ml) was stirred under reflux for 10 hours and cooled to room temperature. The precipitates were collected and washed with tetrahydrofuran to give 4-[[3-ethoxycarbonyl-7-(trifluoromethyl)-4-quinolyl]amino]benzoic acid hydrochloride (2.69 g) as yellow powder.

mp: 256°–257° C. (dec.).

IR (Nujol): 3300–3000, 1735, 1710, 1635 cm$^{-1}$.

NMR (CF$_3$COOH, δ): 1.66 (3H, t, J=7 Hz), 4.68 (2H, quartet, J=7 Hz), 7.45–8.5 (7H, m), 9.4 (1H, m), 12.73 (1H, broad s).

(2) A suspension of 4-[[3-ethoxycarbonyl-7-(trifluoromethyl)-4-quinolyl]amino]benzoic acid hydrochloride (2.51 g) in thionyl chloride (25 ml) was stirred under reflux for 4 hours and concentrated to dryness in vacuo to give 4-[[3-ethoxycarbonyl-7-(trifluoromethyl)-4-quinolyl]amino]benzoyl chloride hydrochloride (2.62 g) as yellow powder.

mp: 202.5°–223° C.

IR (Nujol): 2560 (broad), 1780, 1715, 1620 cm$^{-1}$.

NMR (DMSO-d$_6$, δ): 1.10 (3H, t, J=7 Hz), 3.78 (2H, quartet, J=7 Hz), 7.3–9.3 (8H, m), 11.8 (2H, broad s).

(3) 4-[[3-Ethoxycarbonyl-7-(trifluoromethyl)-4-quinolyl]amino]benzoyl chloride hydrochloride (0.51 g)

was added slowly to a stirred mixture of 4-[(4-fluorophenyl)sulfonyl]piperidine hydrochloride (0.31 g) and triethylamine (0.77 ml) in methylene chloride (8 ml) at room temperature. The resultant mixture was stirred at the same temperature for 2.5 hours and concentrated in vacuo. The residue was partitioned between chloroform and water. The organic layer was washed with saturated aqueous sodium bicarbonate, dried over magnesium sulfate, and concentrated to dryness in vacuo. The oily residue was treated with excess ethanolic hydrochloric acid to give hydrochloride, which was washed with ethanol to give 1-[4-[[3-ethoxycarbonyl-7-(trifluoromethyl)-4-quinolyl]amino]benzoyl]-4-[(4-fluorophenyl)sulfonyl]piperidine hydrochloride (0.67 g) as yellow powder.

mp: 231°–233° C. (dec.).

IR (Nujol): 3120, 2580 (broad), 1730, 1645, 1625, 1300, 1140 cm$^{-1}$.

NMR (CF$_3$COOH, δ): 1.57 (3H, t, J=7 Hz), 1.9–2.5 (4H, m), 3.0–5.25 (5H, m), 4.68 (2H, quartet, J=7 Hz), 7.3–8.3 (10H, m), 8.40 (1H, broad s), 9.45 (1H, broad s), 12.65 (1H, broad s).

EXAMPLE 11

(1) An emulsion of phenyl 4-[2-fluorophenyl)thio]-1-piperidinecarboxylate (32 g) in a mixture of ethanol (317 ml) and 45% potassium hydroxide solution (197 ml) was stirred under reflux for 5 hours. The reaction mixture was evaporated in vacuo and the resultant aqueous mixture was extracted twice with chloroform. The extracts were combined and dried over magnesium sulfate. After removal of magnesium sulfate, the solution was treated with ethanolic hydrochloric acid and concentrated to dryness in vacuo. The residue was washed with ethyl acetate to give 4-[(2-fluorophenyl)thio]piperidine hydrochloride (19.1 g).

mp: 147°–148.5° C. (recrystallized from a mixture of ethyl acetate and isopropanol).

IR (Nujol): 2800–2300 cm$^{-1}$.

NMR (DMSO-d$_6$, δ): 1.25–2.4 (4H, m), 2.85–3.85 (5H, m), 7.0–7.8 (4H, m), 9.35 (2H, broad s).

(2) 4-[[7-(Trifluoromethyl)-4-quinolyl]amino]benzoyl chloride hydrochloride (26.6 g) was added slowly to a stirred mixture of 4-[(2-fluorophenyl)thio]piperidine hydrochloride (17.0 g) and triethylamine (47.7 ml) in dry methylene chloride (350 ml) at room temperature. The resultant mixture was stirred at the same temperature for 3 hours, and concentrated to dryness in vacuo. Water was added to the residue and the precipitated powder was collected by filtration, washed with water and diisopropyl ether, and dried to give a powder (35.5 g). The powder was recrystallized with following solvents to give 4-[(2-fluorophenyl)thio]-1-[4-[[7-(trifluoromethyl)-4-quinolyl]amino]benzoyl]piperidine.

(1) The object compound recrystallized from ethyl acetate

IR (Nujol): 3200 (weak), 3160 (weak), 3070 (weak), 1645 (shoulder), 1630, 1580, 1570 (shoulder), 1530 cm$^{-1}$.

NMR (DMSO-d$_6$, δ): 1.0–2.25 (4H, m), 2.7–4.3 (5H, m), 7.0–8.8 (13H, m), 9.27 (1H, broad s).

X ray diffraction (Target, Cu; Filter, Ni; Voltage 30 KV; Current 10 m A; Time constant, 0.5 second; Scanning speed, 2°/minute; Chart speed 2 cm/minute; Divergence slit, 1°; Receiving slit, 0.15 m m; Scatter slit, 1°):

| | peak No. | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| 2θ (Bragg diffraction angle) | 7.7° | 12.7° | 13.4° | 13.9° | 15.8° | 17.1° | 19.6° | 20.4° | 21.7° | 22.7° | 23.6° | 24.2° | 25.2° |
| I/Io (relative intensity) | 51 | 28 | 32 | 50 | 63 | 87 | 100 | 38 | 54 | 60 | 52 | 41 | 35 |

Thermal analysis [Atmosphere, N$_2$ (30 ml/minute); Sensitivity, DSC±20 m J/S; Heating rate, 10° C./minute]: Phase transition (133° C.)→melt (170° C.)→phase transition→melt (201° C.).

(2) The object compound recrystallized from ethanol

NMR values are the same as those of the above 1).

IR (Nujol): 3350, 3050 (weak), 1610, 1570, 1530 cm$^{-1}$.

X ray diffraction [Analysis condition is the same as that of the above (1)]:

| | peak No. | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| 2θ (Bragg diffraction angle) | 7.6° | 9.4° | 11.1° | 13.7° | 15.4° | 16.6° | 17.0° | 17.7° | 18.7° | 18.9° | 19.2° | 19.9° |
| I/Io (relative intensity) | 9 | 12 | 41 | 23 | 14 | 23 | 20 | 22 | 29 | 61 | 100 | 15 |

| | peak No. | | | | | | | | | | |
|---|---|---|---|---|---|---|---|---|---|---|---|
| | 13 | 14 | 15 | 16 | 17 | 18 | 19 | 20 | 21 | 22 | 23 |
| 2θ (Bragg diffraction angle) | 20.4° | 21.1° | 21.7° | 22.4° | 23.5° | 24.8° | 26.5° | 27.1° | 27.5° | 28.5° | 29.3° |
| I/Io (relative intensity) | 18 | 58 | 34 | 74 | 15 | 18 | 18 | 20 | 15 | 24 | 13 |

Thermal analysis [Analysis condition is the same as that of the above (1)]: Melt (202° C.).

(3) The object compound recrystallized from acetone

NMR values are the same as those of the above (1).

IR (Nujol): 3160 (weak), 3060 (weak), 1640, 1580, 1535 cm$^{-1}$.

X ray diffraction [Analysis condition is the same as that of the above (1)]:

| | peak No. | | | | | | | | | | |
|---|---|---|---|---|---|---|---|---|---|---|---|
| | 1 | 2 | 3 | 4 | 5 | 6 | 7 | 8 | 9 | 10 | 11 |
| 2θ (Bragg diffraction angle) | 8.0° | 12.7° | 13.5° | 13.9° | 14.4° | 15.6° | 17.1° | 17.5° | 18.5° | 19.7° | 10.1° |
| I/Io (relative intensity) | 95 | 16 | 20 | 20 | 14 | 68 | 44 | 30 | 31 | 100 | 51 |

-continued

|  | peak No. | | | | | | | | | | |
| --- | --- | --- | --- | --- | --- | --- | --- | --- | --- | --- | --- |
|  | 12 | 13 | 14 | 15 | 16 | 17 | 18 | 19 | 20 | 21 | 22 |
| 2θ (Bragg diffraction angle) | 10.8° | 11.3° | 11.8° | 13.3° | 14.3° | 15.2° | 15.6° | 16.4° | 18.0° | 18.3° | 19.5° |
| I/Io (relative intensity) | 28 | 38 | 26 | 51 | 18 | 23 | 21 | 20 | 24 | 18 | 21 |

Thermal analysis [Analysis condition is the same as that of the above (1)]: Melt (172° C.)→phase transition→melt (202° C.).

(3) 4-[(2-Fluorophenyl)thio]-1-[4-[[7-(trifluoromethyl)-4-quinolyl]amino]benzoyl]piperidine (1.34 g) was suspended in methanol. Excess ethanolic hydrochloric acid was added to the suspension and the resulting solution was concentrated in vacuo to give an oil. The oil was triturated in acetone to give 4-[(2-fluorophenyl)thio]-1-[4-[[7-(trifluoromethyl)-4-quinolyl]amino]benzoyl]piperidine hydrochloride (1.11 g) as a powder.

(1) The hydrochloride recrystallized from a mixture of water and acetone (1:1)

(a) Crystallization temperature; 30°-40° C.

IR (Nujol): 3130 (weak), 3080 (weak), 3030 (weak), 2700, 1650 (shoulder), 1615 (shoulder), 1590, 1570, 1550 cm⁻¹.

NMR (DMSO-d₆, δ): 1.0-2.2 (4H, m), 2.7-4.4 (5H, m), 6.95-9.3 (13H, m), 11.6 (1H, broad).

X ray diffraction (Target, Cu; Filter, Ni; Voltage 30 KV; Current, 10 m A; Time constant, 0.5 second; Scanning speed, 2°/minute; Chart speed 2 cm/minute; Divergence slit, 1°; Receiving slit, 0.15 m m; Scatter slit, 1°):

NMR values are the same as those of the above (a).

IR (Nujol): 3430 (weak), 3200 (weak), 3030 (weak), 2680, 1620, 1595, 1530 cm⁻¹.

X ray diffraction [Analysis condition is the same as that of the above (a)]:

|  | peak number | | | | | | | | | | | | | |
| --- | --- | --- | --- | --- | --- | --- | --- | --- | --- | --- | --- | --- | --- | --- |
|  | 1 | 2 | 3 | 4 | 5 | 6 | 7 | 8 | 9 | 10 | 11 | 12 | 13 | 14 |
| 2θ (Bragg diffraction angle) | 9.7° | 10.8° | 15.4° | 16.8° | 17.3° | 18.7° | 19.6° | 20.2° | 21.8° | 22.8° | 24.0° | 25.4° | 28.0° | 29.4° |
| I/Io (relative intensity) | 34 | 34 | 45 | 66 | 69 | 100 | 79 | 69 | 55 | 45 | 90 | 59 | 45 | 38 |

The thermal Analysis [Analysis condition is the same as that of the above a)]: Phase transition (215°-224° C.)—melt (257° C.).

(2) The hydrochloride recrystallized from ethanol

NMR values are the same as those of the above (1)-(a).

IR (Nujol): 3370 (weak), 3200 (weak), 3030 (weak), 2510, 1640 (shoulder), 1625 (shoulder), 1605, 1590, 1560, 1535 cm⁻¹.

X ray diffraction [Analysis condition is the same as that of the above (1)-(a).

|  | peak No. | | | | | | | | | | | | | | | | | |
| --- | --- | --- | --- | --- | --- | --- | --- | --- | --- | --- | --- | --- | --- | --- | --- | --- | --- | --- |
|  | 1 | 2 | 3 | 4 | 5 | 6 | 7 | 8 | 9 | 10 | 11 | 12 | 13 | 14 | 15 | 16 | 17 | 18 |
| 2θ (Bragg diffraction angle) | 6.7° | 9.3° | 11.4° | 12.4° | 17.1° | 18.7° | 19.2° | 19.9° | 20.2° | 21.6° | 22.0° | 23.5° | 25.1° | 25.7° | 26.8° | 27.7° | 28.3° | 29.4° |
| I/Io (relative intensity) | 46 | 42 | 30 | 51 | 47 | 48 | 54 | 100 | 77 | 41 | 37 | 28 | 99 | 44 | 25 | 38 | 37 | 23 |

Thermal Analysis [Analysis condition is the same as that of the above (1)-(a). Desolvation of ethanol (142° C.)→phase transition→melt (231° C.)→phase transition→melt (257° C.).

(2) The hydrochloride recrystallized from ethanolic hydrochloric acid

NMR values are the same as those of the above (1)-(a).

|  | peak No. | | | | | | | | | |
| --- | --- | --- | --- | --- | --- | --- | --- | --- | --- | --- |
|  | 1 | 2 | 3 | 4 | 5 | 6 | 7 | 8 | 9 | 10 |
| 2θ (Bragg diffraction angle) | 7.7° | 8.8° | 11.5° | 15.9° | 16.3° | 17.6° | 18.1° | 19.3° | 19.9° | 21.0° |
| I/Io (relative intensity) | 17 | 19 | 42 | 30 | 30 | 84 | 41 | 27 | 42 | 100 |

|  | peak No. | | | | | | | | | |
| --- | --- | --- | --- | --- | --- | --- | --- | --- | --- | --- |
|  | 11 | 12 | 13 | 14 | 15 | 16 | 17 | 18 | 19 | 20 |
| 2θ (Bragg diffraction angle) | 21.8° | 22.8° | 23.6° | 25.0° | 25.8° | 27.1° | 28.1° | 28.3° | 28.7° | 29.3° |
| I/Io (relative intensity) | 22 | 32 | 22 | 22 | 37 | 30 | 20 | 19 | 22 | 19 |

Thermal analysis (Atmosphere, N₂ (30 ml/minute); Sensitivity, DSC±20 m J/S; Heating rate 10° C./minute]: Melt (258° C.).

(b) Crystallization temperature; 0°-30° C.

IR (Nujol): 3200 (weak), 3140 (weak), 3040 (weak), 2710, 1625, 1595, 1565, 1540 cm⁻¹.

X ray diffraction [Analysis condition is the same as that of the above (1)-(a)]:

|  | peak No. | | | | | | | | | | | | | | | |
| --- | --- | --- | --- | --- | --- | --- | --- | --- | --- | --- | --- | --- | --- | --- | --- | --- |
|  | 1 | 2 | 3 | 4 | 5 | 6 | 7 | 8 | 9 | 10 | 11 | 12 | 13 | 14 | 15 |
| 2θ (Bragg diffraction angle) | 7.5° | 8.4° | 9.7° | 11.5° | 12.1° | 12.7° | 13.1° | 15.3° | 15.9° | 16.4° | 17.1° | 17.6° | 17.9° | 18.1° | 18.5° |
| I/Io (relative intensity) | 19 | 13 | 15 | 16 | 23 | 27 | 26 | 23 | 18 | 18 | 35 | 42 | 42 | 34 | 40 |

| | peak No. | | | | | | | | | | | | | |
|---|---|---|---|---|---|---|---|---|---|---|---|---|---|---|
| | 16 | 17 | 18 | 19 | 20 | 21 | 22 | 23 | 24 | 25 | 26 | 27 | 28 | 29 | 30 |
| 2θ (Bragg diffraction angle) | 19.4° | 21.1° | 21.4° | 21.9° | 22.6° | 22.9° | 24.1° | 24.3° | 24.9° | 25.4° | 26.8° | 27.2° | 28.1° | 28.7° | 29.5° |
| I/Io (relative intensity) | 94 | 47 | 79 | 100 | 39 | 24 | 23 | 26 | 24 | 21 | 23 | 24 | 34 | 24 | 28 |

Thermal Analysis [Analysis condition is the same as that of the above (1)-(a)]: Melt (267° C.).

EXAMPLE 12

(1) 3-Chloroperbenzoic acid (0.76 g) was slowly added to a stirred solution of 4-[(2-fluorophenyl)thio]-piperidne hydrochloride (0.95 g) in a mixture of chloroform (71 ml) and methanol (4 ml) under ice-cooling over a period of 5 minutes and the reaction mixture was stirred at the same temperature for 1 hour. After being treated with sodium bisulfate solution under ice-cooling, the resultant mixture was adjusted to alkaline pH with 20% sodium hydroxide solution. The chloroform layer was separated and the aqueous layer was extracted three times with chloroform. The chloroform layers were combined and dried over magnesium sulfate. After removal of magnesium sulfate, the solution was treated with ethereal hydrochloric acid and concentrated to dryness in vacuo. The residue was washed with isopropanol to give 4-[(2-fluorophenyl)sulfinyl]-piperidine hydrochloride (0.48 g).

mp: 209°-210° C.

IR (Nujol): 2850-2400, 1045 cm$^{-1}$.

NMR (DMSO-d$_6$, δ): 1.15-2.35 (4H, m), 2.75-3.7 (5H, m), 7.0-8.0 (4H, m), 8.85-9.65 (2H, broad s).

(2) The following compound was prepared in a similar manner to that of Example 3 (2).

4-[(2-Fluorophenyl)sulfinyl]-1-[4-[[7-(trifluoromethyl)-4-quinolyl]amino]benzoyl]piperidine.

mp: 221°-222° C.

IR (Nujol): 3325, 1615, 1570, 1040 cm$^{-1}$.

NMR (CDCl$_3$-CD$_3$OD, δ): 1.5-2.2 (4H, m), 2.8-3.23 (3H, m), 4.0-4.7 (2H, m), 7.1-8.67 (13H, m).

EXAMPLE 13

(1) The following compound was prepared in a similar manner to that of Example 1 (3).

Phenyl 4-[(2-thienyl)sulfonyl]-1-piperidinecarboxylate.

IR (Film): 1715, 1700, 1310, 1140 cm$^{-1}$.

NMR (DMSO-d$_6$, δ): 1.15-2.25 (4H, m), 2.8-4.0 (3H, m), 4.1-4.65 (2H, m), 7.1-8.4 (8H, m).

(2) An emulsion of phenyl 4-[(2-thienyl)sulfonyl]-1-piperidine carboxylate (1.7 g) in a mixture of ethanol (39.8 ml) and 45% potassium hydroxide solution (24.5 ml) was stirred under reflux for 1.5 hours. Most of the ethanol was evaporated in vacuo and the resultant aqueous mixture was extracted three times with methylene chloride. The extracts were combined and dried over magnesium sulfate. After removal of magnesium sulfate, the solution was treated with ethanolic hydrochloric acid and concentrated to dryness in vacuo. The residue was washed with isopropanol to give 4-[(2-thienyl)sulfonyl]piperidine hydrochloride (1.17 g).

mp: 244°-246° C.

IR (Nujol): 2800-2300, 1340, 1140 cm$^{-1}$.

NMR (D$_2$O, δ): 1.65-2.65 (4H, m), 2.65-3.35 (2H, m), 3.35-4.0 (3H, m), 7.2-7.65 (1H, m), 7.75-8.25 (2H, m).

(3) The following compound was prepared in a similar manner to that of Example 4 (4).

4-[(2-Thienyl)sulfonyl]-1-[4-[[7-(trifluoromethyl)-4-quinolyl]amino]benzoyl]piperidine hydrochloride.

mp: 206°-210° C. (recrystallized from ethanol).

IR (Nujol): 2700-2300, 1640, 1600, 1330, 1140 cm$^{-1}$.

NMR (CDCl$_3$-CD$_3$OF, δ): 1.5-2.4 (4H, m), 2.75-3.65 (3H, m), 3.85-4.4 (2H, m), 7.0-9.15 (13H, m).

EXAMPLE 14

(1) The following compound was prepared in a similar manner to that of Example 1 (1).

1-Methyl-4-[(2-thienyl)thio]piperidine.

IR (film): 3070, 3000-2700 cm$^{-1}$.

NMR (CDCl$_3$, δ): 1.4-2.0 (6H, m), 2.2 (3H, s), 2.3-3.15 (3H, m), 6.85-7.5 (3H, m).

(2) The following compound was prepared in a similar manner to that of Example 1 (2).

Phenyl 4-[(2-thienyl)thio]-1-piperidine-carboxylate.

IR (film): 1740-1720 cm$^{-1}$.

NMR (CDCl$_3$, δ): 1.35-2.5 (4H, m), 2.85-3.5 (3H, m), 4.0-4.5 (2H, m), 7.0-7.65 (8H, m).

(3) The following compound was prepared in a similar manner to that of Example 13 (2).

4-[(2-Thienyl)thio]piperidine hydrochloride.

mp: 175°-177° C.

IR (Nujol): 2800-2300 cm$^{-1}$.

NMR (DMSO-d$_6$, δ): 1.4-2.35 (4H, m), 2.65-3.55 (5H, m), 7.0-7.4 (2H, m), 7.65-7.85 (1H, m), 9.15 (2H, broad s).

(4) The following compound was prepared in a similar manner to that of Example 3 (2).

4-[(2-Thienyl)thio]-1-[4-[[7-(trifluoromethyl)-4-quinolyl]amino]benzoyl]piperidine.

mp: 218.5°-221° C.

IR (Nujol): 3300, 1620, 1610, 1580 cm$^{-1}$.

NMR (DMSO-d$_6$, δ): 1.0-2.35 (4H, m), 2.85-3.1 (3H, m), 3.75-4.35 (2H, m), 7.0-8.85 (12H, m), 9.33 (1H, s).

EXAMPLE 15

(1) The following compound was prepared in a similar manner to that of Example 3 (1).

4-[(2-Thienyl)sulfinyl]piperidine hydrochloride.

mp: 203°-205° C.

IR (Nujol): 2800-2350, 1040 cm$^{-1}$.

NMR (DMSO-d$_6$, δ): 1.35-2.25 (4H, m), 2.65-3.35 (5H, m), 7.25 (1H, m), 7.55 (1H, m), 7.99 (1H, m), 9.27 (2H, broad s).

(2) The following compound was prepared in a similar manner to that of Example 3 (2).

4-[(2-Thienyl)sulfinyl]-1-[4-[[7-(trifluoromethyl)-4-quinolyl]amino]benzoyl]piperidine.

mp: 220°-221.5° C. (recrystallized from methanol)

IR (Nujol): 3230, 3160, 1620, 1580, 1020 cm$^{-1}$.

NMR (CDCl$_3$-CD$_3$OD, δ): 1.4-2.35 (4H, m), 2.9-3.5 (3H, m), 4.0-4.5 (2H, m), 7.1-8.65 (12H, m).

EXAMPLE 16

(1) m-Chloroperbenzoic acid (1.20 g) was added to a stirred solution of 4-[(4-pyridyl)thio]piperidine dihydrochloride (1.33 g) in water (30 ml) under ice-cooling, and the mixture was stirred at the same temperature for 3 hours and then at room temperature for 5.5 hours. The resultant mixture was diluted with water and the pH of the mixture was adjusted to about 11 with 5% sodium hydroxide solution. The solution was extracted several times with chloroform. The extracts were combined, dried over magnesium sulfate, and concentrated in vacuo. The oily residue was crystallized from n-hexane and the crystals were recrystallized from a mixture of n-hexane and isopropanol to give 4-[(4-pyridyl)sulfinyl]piperidine (0.95 g).

mp: 73°–76° C.
IR (Nujol): 3300, 3200, 1045 cm$^{-1}$.
NMR (CDCl$_3$, δ): 1.5–3.4 (10H, m), 7.4–9.0 (4H, m).

(2) The following compound was prepared in a similar manner to that of Example 6 (4).

4-[(4-Pyridyl)sulfinyl]-1-[4-[[7-(trifluoromethyl)-4-quinolyl]amino]benzoyl]piperidine.

mp: 196°–198° C. (recrystallized from a mixture of isopropanol and ethanol).
IR (Nujol): 3330, 1615, 1570, 1040 cm$^{-1}$.
NMR (DMSO-d$_6$, δ): 1.5–2.2 (4H, m), 3.0–4.5 (5H, m), 7.1–9.3 (14H, m).

EXAMPLE 17

The following compound was prepared in a similar manner to that of Example 4 (4).

4-[(2-Pyridyl)thio]-1-[4-[[7-(trifluoromethyl)-4-quinolyl]amino]benzoyl]piperidine dihydrochloride.

mp: 248°–251° C.
IR (Nujol): 2650 (broad), 1620, 1610, 1600 cm$^{-1}$.
NMR (D$_2$O, δ): 1.15–2.65 (4H, m), 3.0–4.65 (5H, m), 7.0–8.75 (13H, m).

EXAMPLE 18

(1) A mixture of 4-[(2-pyridyl)thio]piperidine dihydrochloride (1.0 g) and 30% hydrogen peroxide (10 ml) in acetic acid (15 ml) was stirred at room temperature for 20 minutes and at 70° C. for 2.5 hours. The mixture was treated with excess sodium sulfite solution and concentrated in vacuo. The residue was diluted with water, adjusted to alkaline pH with 5N aqueous potassium hydroxide solution, and extracted three times with chloroform. The extracts were combined, dried over magnesium sulfate, and concentrated in vacuo. The oily residue was dissolved in chloroform and treated with ethanolic hydrochloric acid. The solution was concentrated to dryness in vacuo. The solid residue was washed with isopropanol to give 4-[(2-pyridyl)sulfonyl]piperidine hydrochloride (0.84 g).

mp: 246.5°–248° C.
IR (Nujol): 2800–2500, 2450, 1330, 1140 cm$^{-1}$.
NMR (CDCl$_3$-CD$_3$OD, δ): 2.0–2.65 (4H, m), 2.85–4.0 (5H, m), 7.45–7.85 (1H, m), 8.0–8.35 (2H, m), 8.65–8.95 (1H, m).

(2) The following compound was prepared in a similar manner to that of Example 4 (4).

4-[(2-Pyridyl)sulfonyl]-1-[4-[[7-(trifluoromethyl)-4-quinolyl]amino]benzoyl]piperidine hydrochloride.

mp: 193° C. (dec.)
IR (Nujol): 2750–2300, 1620, 1600, 1330, 1140 cm$^{-1}$.
NMR (CF$_3$COOH, δ): 1.7–2.85 (4H, m), 3.0–5.35 (5H, m), 7.0–9.85 (13H, m).

EXAMPLE 19

(1) 1-Benzyl-4-(4-fluorophenoxy)piperidine hydrochloride (3.85 g) was converted to the corresponding free base by treatment with sodium hydroxide solution and extraction with methylene chloride. Phenyl chlorocarbonate (2.8 g) was added dropwise to a stirred solution of the free base in dry methylene chloride (38.5 ml) under ice-cooling. The mixture was stirred at room temperature for 2 hours, washed successively with 1N sodium hydroxide solution, 1N hydrochloric acid, and brine, dried over magnesium sulfate, and concentrated in vacuo. The residue was washed with diethyl ether to give phenyl 4-(4-fluorophenoxy)-1-piperidine carboxylate (2.18 g).

mp: 98.5°–100.5° C.
IR (Nujol): 1730, 1700 cm$^{-1}$.
NMR (DMSO-d$_6$, δ): 1.35–1.4 (4H, m), 3.1–4.15 (4H, m), 4.35–4.85 (1H, m), 6.9–7.65 (9H, m).

(2) The following compound was prepared in a similar manner to that of Example 13 (2).

4-(4-Fluorophenoxy)piperidine hydrochloride.
mp: 155°–156° C. (recrystallized from a mixture of diisopropyl ether and isopropanol).
IR (Nujol): 2800–2300, 1220 cm$^{-1}$.

(3) The following compound was prepared in a similar manner to that of Example 4 (4).

4-(4-Fluorophenoxy)-1-[4-[[7-(trifluoromethyl)-4-quinolyl]amino]benzoyl]piperidine hydrochloride.
mp: 260°–263° C. (recrystallized from ethanol).
IR (Nujol): 2700, 1620, 1590 cm$^{-1}$.
NRM (DMSO-d$_6$, δ): 1.35–2.3 (4H, m), 3.0–4.3 (4H, m), 4.5–5.0 (1H, m), 7.05–9.4 (13H, m).

EXAMPLE 20

The following compound was prepared in a similar manner to that of Example 4 (4).

4-[(4-Fluorophenyl)amino]-1-[4-[[7-(trifluoromethyl)-4-quinolyl]amino]benzoyl]piperidine dihydrochloride.

mp: 212.5°–215° C. (recrystallized from a mixture of ethyl acetate and ethanol).
IR (Nujol): 2850–2300, 1620, 1600 cm$^{-1}$.
NMR (CDCL$_3$-CD$_3$OD, δ): 1.65–2.5 (4H, m), 2.65–4.4 (5H, m), 7.0–9.2 (13 H, m).

EXAMPLE 21

The following compound was prepared in a similar manner to that of Example 6 (4).

1-[4-[[3-Ethoxycarbonyl-7-(trifluoromethyl)-4-quinolyl]amino]benzoyl]-4-[(4-fluorophenyl)thio]-piperidine.

mp: 129.5°–132.5° C. (recrystallized from a mixture of n-hexane and ethyl acetate).
IR (Nujol): 3240, 3180, 1680, 1630 cm$^{-1}$.
NMR (CDCl$_3$, δ): 1.47 (3H, t, J=7 Hz), 1.15–2.2 (4H, m), 2.55–3.45 (3H, m), 3.85–4.5 (2H, m), 4.46 (2H, quartet, J=7 Hz), 6.8–7.55 (9H, m), 7.77 (1H, d, J=8 Hz), 8.29 (1H, s), 9.31 (1H, s), 10.47 (1H, s).

EXAMPLE 22

The following compound was prepared in a similar manner to that of Example 6 (4).

1-[4-[[3-Ethoxycarbonyl-7-(trifluoromethyl)-4-quinolyl]amino]benzoyl]-4-[(4-fluorophenyl)sulfinyl]-piperidine.

mp: 162°–165° C. (recrystallized from a mixture of diisopropyl ether and ethyl acetate).
IR (Nujol): 3230, 3170, 1680, 1620, 1595, 1035 cm$^{-1}$.
NMR (CDCl$_3$, δ): 1.47 (3H, t, J=7 Hz), 1.6–2.0 (4H, m), 2.45–3.1 (3H, m), 4.15–4.5 (2H, m), 4.44 (2H, quartet, J=7 Hz), 6.95–7.85 (10H, m), 8.33 (1H, s), 9.37 (1H, s), 10.5 (1H, s).

EXAMPLE 23

The following compounds were prepared in a similar manner to that of Example 8 (4).

(1) 4-[2-Fluorophenyl)sulfonyl]-1-[4-[[7-(trifluoromethyl)-4-quinolyl]amino]benzoyl]piperidine hydrochloride.

IR (Nujol): 3220-3040 (m), 2500 (broad), 1610, 1590, 1320, 1150 cm$^{-1}$.

(2) 4-[(4-Fluorophenyl)thio]-1-[4-[[7-(trifluoromethyl)-4-quinolyl]amino]benzoyl]piperidine.

IR (Nujol): 3300, 1610 cm$^{-1}$.

(3) 4-[(4-Fluorophenyl)sulfinyl]-1-[4-[[7-(trifluoromethyl)-4-quinolyl]amino]benzoyl]piperidine.

IR (Nujol): 3320, 1615, 1565, 1040 cm$^{-1}$.

(4) 4-[(4-Pyridyl)thiol]-1-[4-[[7-(trifluoromethyl)-4-quinolyl]amino]benzoyl]piperidine dihydrochloride.

IR (Nujol): 2560, 1620, 1590 cm$^{-1}$.

(5) 4-[(4-Pyridyl)sulfonyl]-1-[4-[[7-(trifluoromethyl)-4-quinolyl]amino]benzoyl]piperidine dihydrochloride.

IR (Nujol): 1620, 1600, 1325, 1155, 1130 cm$^{-1}$.

(6) 4-[(2-Pyridyl)sulfinyl]-1-[4-[[7-(trifluoromethyl)-4-quinolyl]amino]benzoyl]piperidine.

IR (Nujol): 3325, 1610, 1565, 1040 cm$^{-1}$.

(7) 4-Benzyl-1-[4-[[7-(trifluoromethyl)-4-quinolyl]-amino]benzoyl]piperidine hydrochloride.

IR (Nujol): 3200-3020, 2550 (broad), 1635, 1620, 1590 cm$^{-1}$.

(8) 4-[(4-Fluorophenyl)sulfonyl]-1-[4-[[7-(trifluoromethyl)-4-quinolyl]amino]benzoyl]piperidine hydrochloride.

IR (Nujol): 2650 (broad), 1635, 1610, 1585, 1320, 1140 cm$^{-1}$.

(9) 1-[4-[[3-Ethoxycarbonyl-7-(trifluoromethyl)-4-quinolyl]amino]benzoyl]-4-[(4-fluorophenyl)sulfonyl]-piperidine hydrochloride.

IR (Nujol): 3120, 2580 (broad), 1730, 1645, 1624, 1300, 1140 cm$^{-1}$.

(10) 4-[(2-Fluorophenyl)thio]-1-[4-[[7-(trifluoromethyl)-4-quinolyl]amino]benzoyl]piperidine.

IR (Nujol): 3670-3150, 1640, 1580 cm$^{-1}$.

(11) 4-[(2-Fluorophenyl)sulfinyl]-1-[4-[[7-(trifluoromethyl)-4-quinolyl]amino]benzoyl]piperidine.

IR (Nujol): 3325, 1615, 1570, 1040 cm$^{-1}$.

(12) 4-[(2-Thienyl)sulfonyl]-1-[4-[[7-(trifluoromethyl)-4-quinolyl]amino]benzoyl]piperidine hydrochloride.

IR (Nujol): 2700-2300, 1640, 1600, 1330, 1140 cm$^{-1}$.

(13) 4-[(2-Thienyl)thio]-1-[4-[[7-(trifluoromethyl)-4-quinolyl]amino]benzoyl]piperidine.

IR (Nujol): 3300, 1620, 1610, 1580 cm$^{-1}$.

(14) 4-[(2-Thienyl)sulfinyl]-1-[4-[[7-(trifluoromethyl)-4-quinolyl]amino]benzoyl]piperidine.

IR (Nujol): 3230, 3160, 1620, 1580, 1020 cm$^{-1}$.

(15) 4-[(4-Pyridyl)sulfinyl]-1-[4-[[7-(trifluoromethyl)-4-quinolyl]amino]benzoyl]piperidine.

IR (Nujol): 3330, 1615, 1570, 1040 cm$^{-1}$.

(16) 4-[(2-Pyridyl)thio]-1-[4-[[7-(trifluoromethyl)-4-quinolyl]amino]benzoyl]piperidine dihydrochloride.

IR (Nujol): 2650 (broad), 1620, 1610, 1600 cm$^{-1}$.

(17) 4-[(2-Pyridyl)sulfonyl]-1-[4-[[7-(trifluoromethyl)-4-quinolyl]amino]benzoyl]piperidine hydrochloride.

IR (Nujol): 2750-2300, 1620, 1600, 1330, 1140 cm$^{-1}$.

(18) 4-(4-Fluorophenoxy)-1-[4-[[7(trifluoromethyl)-4-quinolyl]amino]benzoyl]piperidine.

IR (Nujol): 2700, 1620, 1590 cm$^{-1}$.

(19) 4-[(4-Fluorophenyl)amino]-1-[4-[[7-(trifluoromethyl)-4-quinolyl]amino]benzoyl]piperidine dihydrochloride.

IR (Nujol): 2850-2300, 1620, 1600 cm$^{-1}$.

(20) 1-[4-[[-3-Ethoxycarbonyl-7-(trifluoromethyl)-4-quinolyl]amino]benzoyl]-4-[(4-fluorophenyl)thio]-piperidine.

IR (Nujol): 3240, 3180, 1680, 1630 cm$^{-1}$.

(21) 1-[4-[[3-Ethoxycarbonyl-7-(trifluoromethyl)-4-quinolyl]amino]benzoyl]-4-[(4-fluorophenyl)sulfinyl]-piperidine.

IR (Nujol): 3230, 3170, 1680, 1620, 1595, 1035 cm$^{-1}$.

EXAMPLE 24

Th following compound was prepared in a similar manner to that of Example 1 (5).

4-[(4-fluorophenyl)hydroxymethyl]-1-[4-[[7-(trifluoromethyl)-4-quinolyl]amino]benzoyl]piperidine hydrochloride.

IR(Nujol): 3350, 3340, 2800-2400, 1620, 1600, 1580 cm$^{-1}$.

We claim:

1. A piperidine compound of the formula:

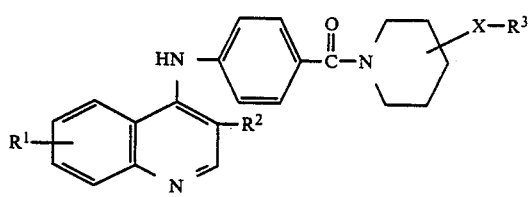

wherein
$R^1$ is hydrogen or trihalomethyl,
$R^2$ is hydrogen or esterified carboxy,
$R^3$ is 5 or 6-membered heteromonocyclic aryl having group a nitrogen or sulfur atom or phenyl, tolyl or naphthyl which may be mono-halogen substituted and
X is

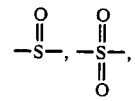

or —S—, or pharmaceutically acceptable salt thereof.

2. A piperidine compound according to claim 1 which is represented by the formula:

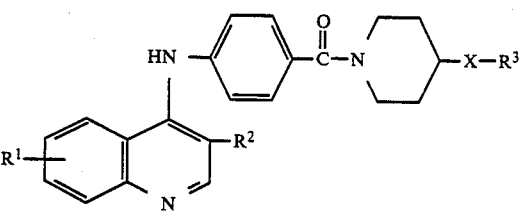

wherein $R^2$, $R^3$ and X are each as defined in claim 1, and $R^1$ is trihalomethyl, or pharmaceutically acceptable salt thereof.

3. A piperidine compound according to claim 2, in which $R^1$ and X are each as defined in claim 2, $R^2$ is hydrogen or esterified carboxy and $R^3$ is 5 or 6-membered heteromonocyclic group containing a nitrogen or sulfur atom or phenyl which may be monohalogen substituted.

4. A piperidine compound according to claim 3, in which $R^1$ and X are each as defined in claim 3, $R^2$ is hydrogen or lower alkoxycarbonyl and $R^3$ is pyridyl, thienyl or phenyl which may be monohalogen substituted.

5. A piperidine compound according to claim 4, in which
$R^1$ is trifluoromethyl,
$R^2$ is hydrogen or ethoxycarbonyl,
$R^3$ is pyridyl, thienyl or fluorophenyl and
X is —S—,

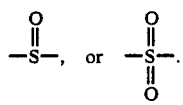

6. A piperidine compound according to claim 5, in which
$R^1$ is trifluoromethyl,
$R^2$ is hydrogen,
$R^3$ is fluorophenyl and
X is —S— or

7. A piperidine compound according to claim 6, which is 4-[(2-fluorophenyl)thio]-1-[4-[[7-(trifluoromethyl)-4-quinolyl]amino]benzoyl]piperidine or pharmaceutically acceptable salt thereof.

8. A piperidine compound according to claim 6, which is 4-[(2-fluorophenyl)sulfonyl]-1-[4-[[7-(trifluoromethyl)-4-quinolyl]amino]benzoyl]piperidine or pharmaceutically acceptable salt thereof.

9. A pharmaceutical composition comprising, as an effective ingredient, one or more piperidine compound(s) of claim 1 or salt(s) thereof and pharmaceutically acceptable carrier(s).

10. The method of causing an antihypertensive effect in a mammal which comprises administering thereto an antihypertensive effective amount of the piperidine compound of claim 1.

* * * * *